United States Patent [19]

Rossmoore et al.

[11] Patent Number: 5,364,649
[45] Date of Patent: Nov. 15, 1994

[54] ANTIMICROBIAL MIXTURES AND METHOD OF USE

[76] Inventors: Leonard A. Rossmoore, 25323 Parkwood, Huntington Woods, Mich. 48070; Harold W. Rossmoore, 4341 Foxpointe Dr., West Bloomfield, Mich. 48323

[21] Appl. No.: 39,845

[22] Filed: Mar. 30, 1993

[51] Int. Cl.$^5$ .................... A01N 59/20; A01N 43/32; A01N 43/68; A01N 43/74
[52] U.S. Cl. .................. 424/637; 514/237.8; 514/241; 514/372; 514/374; 514/499; 514/452; 514/500; 514/697
[58] Field of Search .................. 252/11.36; 514/372, 514/241, 237.8, 452, 374; 424/637

[56] References Cited

U.S. PATENT DOCUMENTS

| | | | |
|---|---|---|---|
| 4,129,509 | 12/1978 | Maurer et al. | 252/49.5 |
| 4,608,183 | 8/1986 | Rossmoore | 252/36 |
| 4,666,616 | 5/1987 | Rossmoore | 252/11 |
| 4,707,282 | 11/1987 | Rossmoore | 252/11 |
| 4,708,808 | 11/1987 | Rossmoore | 252/36 |

OTHER PUBLICATIONS

Tauler, R., et al., Inorg. Chem. Acta: 105(2): 165–170 (1985).
Intl. Biodetn. 26: 303–313, 1990.
Intl. Biodetn. 26:51–61, 1990.
Europ. J. Biochem. 62:151–160 (1976).
Klopotek et al. "Preservation for water-based metal working . . . " CA110:176483p, 1985 (corresponds to Polish Pat. 131755, 30 Dec. 1985).
Rossmore (I) "The Interaction of Formaldehyde Isothiozolone and Copper", International Biodeterioration (26), (1990) (pp. 225–235).

Primary Examiner—Allen J. Robinson
Assistant Examiner—Brian G. Bembenick
Attorney, Agent, or Firm—Ian C. McLeod

[57] ABSTRACT

The activity of antimicrobial compounds selected from isothiazolones and compounds which release formaldehyde is enhanced with a metal complex of a lower alkanolamine, particularly copper (cupric) triethanolamine. The enhancement is particularly useful in metalworking fluids.

14 Claims, 2 Drawing Sheets

ANTIMICROBIAL MIXTURES AND METHOD OF USE

BACKGROUND OF THE INVENTION

1. Field of the Invention

Antimicrobial compounds which interact with environmental and/or cell nucleophiles are potentiated by one or more transition metals mixed with a trilower alkanolamine. The antimicrobial compounds include isothiazolones, preferably alkyl and chloroalkyl 4-isothiazolin-3-one, benzylisothiazolone and n-octyl-4-isothiazolin-3-one alone or in admixture, and also compounds referred to as formaldehyde condensates whose biocidal properties are in part or wholly related to released formaldehyde. The metals are preferably used in the form of a polyfunctional ligand, namely a 1:1 molar complex of the metal with triethanolamine. This complex, which is stable at a broad pH range, effectively delivers the metal cation to nucleophiles, usually amine and/or sulfhydryl compounds (particularly peptides and amino acids) which are produced by the microorganism or are components of the system being protected and which prevent interaction of the microorganism with the antimicrobial agent. The result is prolonged and increased efficacy. Other metal complexes with a trilower alkanolamine can be used.

2. Description of Related Art.

Disodium monocopper (II) citrate is a polyfunctional ligand in which the Cu-ligand bond is via oxygen (Maurer and Shringapurey, U.S. Pat. No. 4,129,509 (1978) on copper citrate; and Tauler, R., et al., *Inorg. Chem. Acta:* 105(2): 165–170 (1985) for copper TEA). Also U.S. Pat. Nos. 4,666,616, 4,608,183, 4,707,282, and 4,708,808 to Rossmoore describe the use of citrate complexes as the polyfunctional ligands.

Distinctions are made between the potentiation of isothiazolone derivatives (U.S. Pat. No. 4,608,183; *Intl. Biodetn.* 26: 303-313, 1990) in which the biocides are irreversibly inactivated by nucleophiles and the formaldehyde-based biocides (U.S. Pat. No. 4,666,616; *Intl. Biodetn.* 26:51-61, 1990; *Europ. J. Biochem.* 62:151-160) in which the enzyme degrading formaldehyde is blocked. In the former the transition metal cation protects the isothiazolone molecule from inactivation by non-critical nucleophiles in and outside the microbial cell allowing the biocide to react with critical nucleophilic sites on the microorganism resulting in lethality. The above referenced patents show that a metal polyfunctional ligand has an advantage over the naked metal cation because of greater stability at neutral and alkaline pHs. The insolubility of the metal hydroxides reduces or eliminates the activity of the metal ions.

OBJECTS

The objects of this invention are to extend the range of transition metals beyond copper and to demonstrate improved polyfunctional ligand-complexes that are more stable than copper (cupric) citrate. Further, it is an object of the present invention to provide complexes which are simple and economical to prepare. These and other objects will become increasingly apparent by reference to the following description and the drawings.

BRIEF DESCRIPTION OF THE DRAWINGS

FIG. 2 shows the stability over a wide pH range for the copper ethanolamine complex.

DESCRIPTION OF PREFERRED EMBODIMENTS

Figure 1:
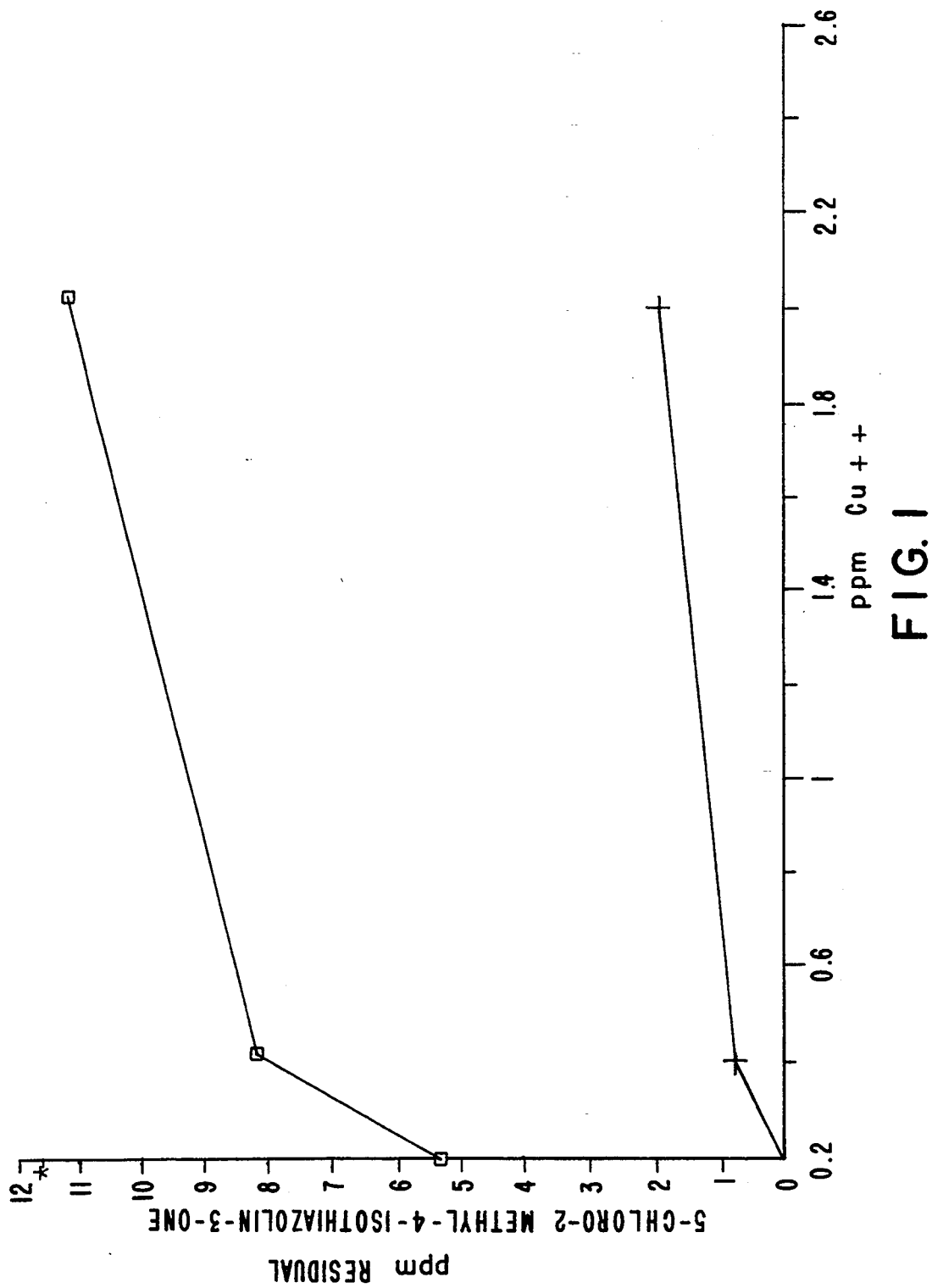
FIG. 1 is a graph showing the protective effects of the use of copper (cupric) triethanolamine (boxes) and copper citrate (crosses) at various concentrations with 5-chloro-2-methyl-4-isothiazolin-3-one (ppm). Cysteine (0.2 mM) was used as a nucleophile in the solution and the concentration of the isothiazolone held in the presence of the cysteine was determined by high pressure liquid chromatography (HPLC).

The present invention relates to a composition which suppresses growth of microorganisms which comprises: an antimicrobial agent selected from the group consisting of an isothiazolone and a compound which releases formaldehyde; a metal ion; and a trilower alkanol amine wherein alkyl is between 1 and 6 carbon atoms and wherein the metal ion and alkanolamine form a complex in the solution which enhances suppression of the microorganisms in a solution by the antimicrobial agent.

The present invention relates to a method for providing a solution which suppresses growth of microorganisms in the solution because of an antimicrobial agent selected from the group consisting of an isothiazolone and a compound which releases formaldehyde in the solution, the improvement which comprises: providing in the solution (1) a metal ion and (2) a trilower alkanolamine wherein alkyl is between 1 and 6 carbon atoms and wherein (1) and (2) form a complex in the solution which enhances suppression of the microorganisms in the solution by the antimicrobial agent.

Biocides which release formaldehyde include: 1,3,5-tris(2-hydroxyethyl)hexahydro-s-triazine; oxozolidines; n-methylolchloroacetamide; 1,3,5-tris(ethyl)hexahydro-s-triazine; 4,4'(2-ethyl-2-nitrotrimethylene)dimorpholine; 4-(2-nitrobutyl)morpholine; tris(hydroxymethyl)-nitromethane; 6-acetoxy-2,4-dimethyl-m-dioxane; and 1(3-chloroallyl)-3,4,7-triaza-1-azoniaadamantane chloride for instance. The thiazolones are well known to those skilled in the art and are described in the U.S. patents described in U.S. Pat. No. 4,608,183.

The trilower alkanolamine is preferably triethanolamine. Other homologs where alkyl is 1 to 6 carbon atoms can be used so long as an effective metal complex is formed. Preferably the amount of the trilower alkylamine is at least sufficient to form a complex with the metal ion.

The metal ion is preferably copper. Other metal ions are, for instance, cobalt, manganese, iron, gold, silver and mercury, since these metals are effective with the isothiazolones or the compounds which release formaldehyde to produce suppression of the growth of the microorganisms. The metal ion is preferably used in an amount between about 1 and 200 ppm in the solution.

The antimicrobial agent is preferably used in an amount between about 0.1 and 50 ppm in the metal-working solution. The amount selected is that which is sufficient to suppress the growth of the microorganisms.

The present invention particularly relates to the use of a polyfunctional ligand, triethanolamine, and copper II with an isothiazolone or a formaldehyde-condensate biocide. The ingredient can be added separately or as a mixture or as the polyfunctional complex to the solution being treated before use.

The solution can be any industrial preparation where microbial contamination control is needed and includes, but not exclusively, metalworking fluids, cooling water, paper pulp slurries, latex suspensions. Preferably the solutions are aqueous.

It has been shown (*Intl. Biodetn.* 26: 225-235, 1990) that with the use of a cysteine, an extremely aggressive biological nucleophile, monitoring of isothiazolone protection can be achieved by high pressure liquid chromatography (HPLC). As will be described in more detail, there is direct correlation between chemical stabilization, as presented by high pressure liquid chromatography (HPLC) data, and biological synergism that is increased biocidal activity with the isothiazolone or formaldehyde producing compound plus the metal compound.

The first series of experiments (Tables 1 and 2) show the relative protection of the mixed methyl-chloromethyl isothiazolone (IT) by 1 mM transition metal from the activity of 0.2 mM cysteine. All of the transition metals protected IT from nucleophile attack with the noble metals being exceptional. The finding of $Fe^{++}$ being protective in contrast to $Fe^{+++}$ was unexpected. The microbiological results shown in Table 2 confirm and extend the protection shown in Table 1.

TABLE 1

Protection of isothiazolone (5-chloro-2-methyl-4-isothiazolin-3-one) from nucleophilic attack (cysteine 0.2 mM) by transition metals

| Transition Metals (1 mM) | % Protection pH 7 | % Protection pH 9 |
|---|---|---|
| Gold ($AuCl_3$) | 10 | 100 |
| Silver ($NO_3$) | 81 | 71 |
| Copper ($CuSO_4$) | 92 | 94 |
| Zinc ($ZnSO_4$) | 0 | 0 |
| Cadmium ($CdCl_2$) | 0 | 8.3 |
| Mercury ($HgCl_2$) | 100 | 97 |
| Palladium ($PdCl_2$) | 7.7 | 0 |
| Tin ($SnCl_2$) | 0 | 0 |
| Molybdenum ($Na_2MO_4$) | 0 | 0 |
| Cobalt ($CoCl_2$) | 100 | 99 |
| Nickel ($N_1Cl_2$) | 0 | 0 |
| Aluminum ($Al_2SO_4)_3$ | 0 | 0 |
| Tungsten ($Na_2WO_4$) | 0 | 0 |
| Lead Pb ($NO_3)_2$ | 0 | 0 |
| Titanium ($TiO_2$) | 0 | 0 |
| Chromium ($K_2Cr_2O_7$) | 0 | 0 |
| Manganese ($MnCl_2$) | 0 | 4.5 |
| $Fe^{++}$ ($Fe(NH_4)_2 (SO_4)_2$) | 18 | 95 |
| $Fe^{+++}$ ($FeCl_3$) | 0 | 0 |

Not unexpected were results with Ag, Au, and Hg which are active as biocides at the levels employed. It should also be emphasized that all of the metals were used as salts, some of which may be complexed or precipitated in the alkaline metalworking fluid. There is a need for a stable form of the metals. It was apparent that not all the successful metals were practical for exploitation because of current cost. These results are without interference from any nucleophiles.

TABLE 2

Potentiation of isothiazolone by transition metals in 5% metalworking fluid

| IT Level (ppm): | Bacterial CFU/mL | | | |
|---|---|---|---|---|
| | 0 | 1.5 | 3.75 | 7.5 |
| Control | $5 \times 10^7$ | $5 \times 10^7$ | $5 \times 10^7$ | $5 \times 10^7$ |
| No Metal | — | $5 \times 10^7$ | $3 \times 10^6$ | $5 \times 10^3$ |
| 1 mM $Cu^{++}$ | $2 \times 10^6$ | $4 \times 10^5$ | $4 \times 10^2$ | NG |
| 1 mM $Co^{++}$ | $3 \times 10^7$ | $1 \times 10^7$ | NG | NG |
| 1 mM $Mn^{++}$ | $5 \times 10^7$ | $4 \times 10^7$ | NG | NG |
| 1 mM $Fe^{++}$ | $2 \times 10^7$ | $7 \times 10^6$ | NG | NG |
| 1 mM $Au^{+++}$ | NG | NG | NG | NG |
| 1 mM $Ag^{+}$ | NG | NG | NG | NG |
| 1 mM $Hg^{++}$ | NG | NG | NG | NG |

IT = 5-chloro-2-methyl-4-isothiazolin-3-one
NG — no growth

Contaminated (*Pseudomonas* sp.) metalworking fluids were incubated at room temperature for 72 hours with shaking.

Previous success with copper citrate suggested using this compound as a benchmark for comparison with a new compound. Copper (cupric) triethanolamine is an oxygen-bond polyfunctional ligand, as is copper citrate. Triethanolamine has many advantages to recommend it over citrate; it is not readily utilized as sole carbon source for bacterial growth, and it is a constituent of many metalworking fluids as a corrosion inhibitor.

Figure 2:
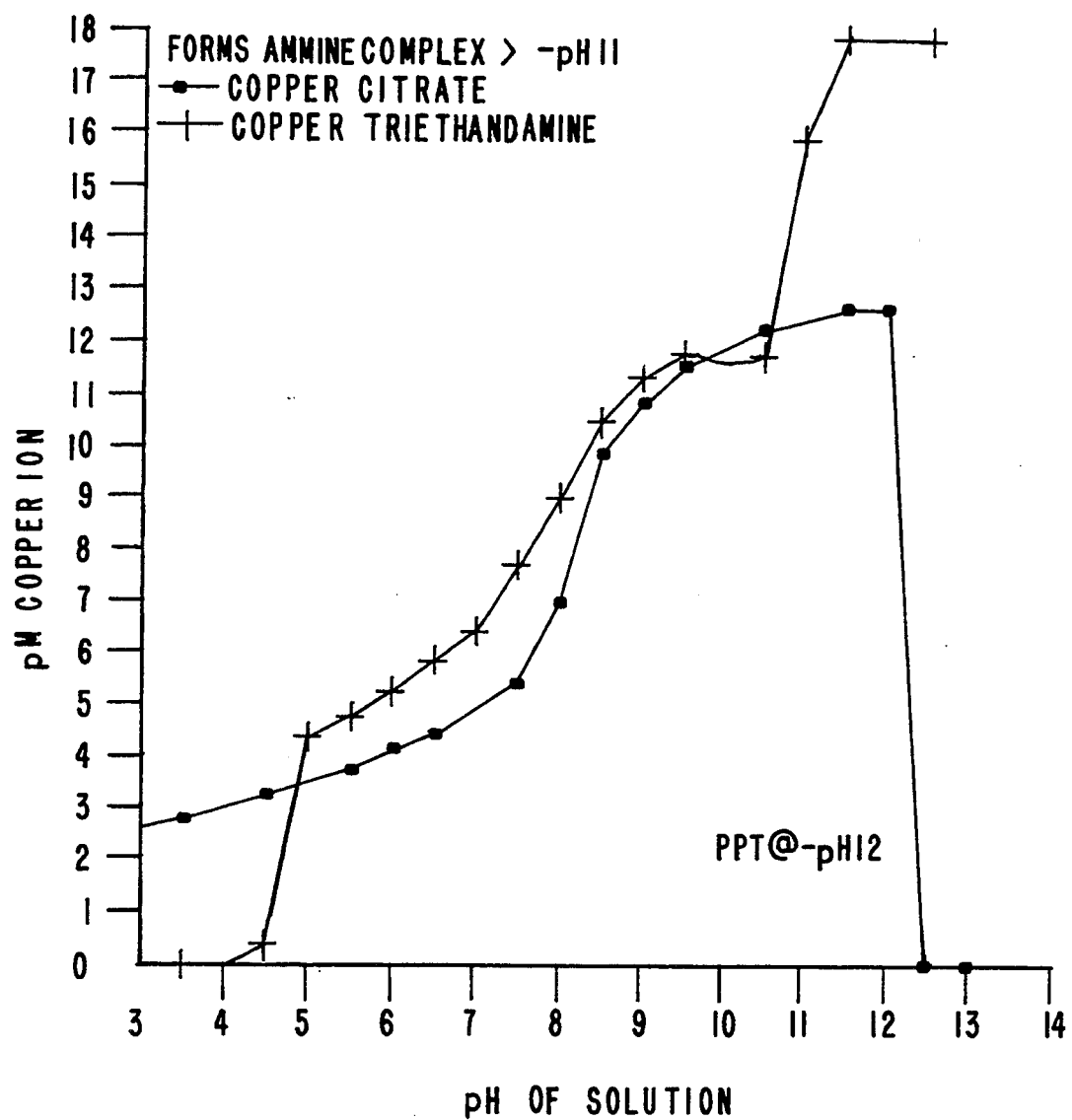
FIG. 2 is a graph showing the copper ion concentration as a function of pH for copper triethanolamine (crosses) and copper citrate (closed boxes).

In FIG. 1 the advantage of copper triethanolamine over copper citrate is shown in protecting isothiazolone from cysteine, a nucleophile. As little as 5 ppm of the complex, equal to 0.2 ppm copper, still protected 50% of isothiazolone, whereas twice as much copper citrate offered no protection. These results were unexpected. FIG. 2 shows the stability of the complex over a wide pH range.

Shown in Tables 3A and 3B are examples of microbiological potentiation with copper triethanolamine ($Cu^2$ TEA). In Table 3A, $Cu^2$ TEA at 20 ppm copper equivalent in nine different randomly selected metalworking fluids (representing the three major types, i.e. soluble oil, semi-synthetic, and synthetic fluids) effectively increased activity of an isothiazolone (IT) biocide in eight of the samples. Table 3A shows the lowest level of biocide and biocide-copper resulting in less than 100 ($10^2$) CFU/mL. This is the limit of sensitivity of the recovery method used.

TABLE 3A

Potentiation of isothiazolone efficacy by copper triethanolamine - 20 ppm copper equivalent in metalworking fluids

| Metalworking fluid (5%) | Bacterial CFU/mL Without Cu | With Cu |
|---|---|---|
| 1. Soluble oil #1 | | |
| 3.75 ppm IT | $4 \times 10^8$ | $<1 \times 10^2$ |
| 11.25 ppm IT | $<1 \times 10^2$ | $<1 \times 10^2$ |
| 2. Soluble oil #2 | | |
| 1.5 ppm IT | $1 \times 10^8$ | $4 \times 10^3$ |
| 3.75 ppm IT | $<1 \times 10^2$ | $<1 \times 10^2$ |
| 3. Soluble oil #3 | | |
| 1.5 ppm IT | $1 \times 10^8$ | $<1 \times 10^2$ |
| 11.25 ppm IT | $<1 \times 10^2$ | $<1 \times 10^2$ |
| 4. Semi-synthetic #1 | | |
| 3.75 ppm IT | $3 \times 10^8$ | $<1 \times 10^2$ |
| 15 ppm IT | $5 \times 10^3$ | $<1 \times 10^2$ |
| 5. Semi-synthetic #2 | | |
| 0 ppm IT | $<1 \times 10^2$ | $3 \times 10^5$ |
| 1.5 ppm IT | $<1 \times 10^2$ | $<1 \times 10^2$ |
| 6. Semi-synthetic #3 | | |
| 1.5 ppm IT | $1 \times 10^8$ | $<1 \times 10^2$ |
| 11.25 ppm IT | $<1 \times 10^2$ | $<1 \times 10^2$ |
| 7. Synthetic #1 | | |
| 1.5 ppm IT | $7 \times 10^8$ | $<1 \times 10^2$ |
| 7.5 ppm IT | $<1 \times 10^2$ | $<1 \times 10^2$ |
| 8. Synthetic #2 | | |
| 1.5 ppm IT | $4 \times 10^8$ | $<1 \times 10^2$ |

TABLE 3A-continued

Potentiation of isothiazolone efficacy by copper triethanolamine - 20 ppm copper equivalent in metalworking fluids

| Metalworking fluid (5%) | Bacterial CFU/mL | |
|---|---|---|
| | Without Cu | With Cu |
| 7.5 ppm IT | $<1 \times 10^2$ | $<1 \times 10^2$ |
| 9. Synthetic #3 | | |
| 7.5 ppm IT | $1 \times 10^3$ | $<1 \times 10^2$ |
| 11.25 ppm IT | $<1 \times 10^2$ | $<1 \times 10^2$ |

IT = 5 chloro-2-methyl-4-isothiazolin-3-one
Table 3B shows the IT remaining after use of the $Cu^2$ TEA.

TABLE 3B

Selected chemical stabilization results (based on HPLC) from Table 3A combinations in metalworking fluid

| Metalworking Fluid | | Residual IT in PPM | | |
|---|---|---|---|---|
| | | Without Copper | With Copper | % Difference |
| #4: | 1.5 ppm IT | 0 | 0.03 | 2 |
| | 3.75 ppm IT | 0 | 1.39 | 40 |
| #2: | 1.5 ppm IT | 0.05 | 0.27 | 14.6 |
| | 3.75 ppm IT | 0.26 | 1.41 | 30 |
| #9: | 1.5 ppm IT | 0 | 0.4 | 2.6 |
| | 3.75 ppm IT | 0.03 | 1.69 | 47 |

IT = 5-chloro-3-methyl-4-isothiazolin-3-one. Levels listed were added at zero time into metalworking fluid.

Table 4 shows the results with a formaldehyde based biocide.

TABLE 4

Potentiation of 1,3,5, Hexahydro-tris (2-hydroxyethyl) triazine by Cu triethanolamine - 20 ppm copper in 5% soluble oil metalworking fluid

| Biocide level (ppm) | Bacterial CFU/mL | |
|---|---|---|
| | Without Copper | With Copper |
| Control (0) | $4 \times 10^7$ | $2 \times 10^6$ |
| 100 | $1 \times 10^8$ | $2 \times 10^7$ |
| 200 | $1 \times 10^8$ | $5 \times 10^4$ |
| 400 | $4 \times 10^5$ | $3 \times 10^5$ |
| 600 | $4 \times 10^5$ | $<1 \times 10^2$ |

Spoiled fluid (Pseudomonas sp.) from the field was incubated with shaking for 72 hours after addition of biocide and $Cu^{++}$ These results essentially confirm for $Cu^2$ TEA.

In Tables 5 and 6 show two aspects of potentiation involving preferential nucleophilic interaction. Table 5 shows the use of $Cu^2$ TEA to increase the antibacterial activity of n-octyl isothiazolone.

TABLE 5

Potentiation of n-octyl isothiazolone antimicrobial activity by copper triethanolamine*

| Biocide Level (ppm) | Without Copper | With Copper |
|---|---|---|
| | Bacterial CFU/mL | |
| 0.5 | $>1 \times 10^7$ | $1 \times 10^6$ |
| 1.25 | $>1 \times 10^7$ | $2 \times 10^5$ |
| 2.5 | $1 \times 10^7$ | $5 \times 10^4$ |
| 5 | $>1 \times 10^7$ | $2 \times 10^4$ |
| | Fungal CFU/mL | |
| 0.5 | $>1 \times 10^4$ | $>1 \times 10^4$ |
| 1.25 | $>1 \times 10^4$ | $>1 \times 10^4$ |
| 2.5 | $>1 \times 10^4$ | $>1 \times 10^4$ |
| 5 | $>1 \times 10^4$ | $3 \times 10^3$ |

*20 ppm copper equivalent. The fungus was __.

These results were not expected since the n-octyl derivative is not considered an antibacterial agent, but rather one directed against fungi.

Table 6 shows an increase in antifungal activity with a formaldehyde-releasing compound with added methyl chloroisothiazolone. The latter biocide formulation was reported in "Interaction of Formaldehyde, Isothiazolone, and Copper" (Intl. Biodetn. 26: 225–235, 1990).

TABLE 6

Potentiation of n-octyl isothiazolone antifungal activity by 1,3,5, hexahydro-tris (2-hydroxyethyl)triazine - 800 ppm

| Biocide Level (ppm) | Bacterial CFU/mL | |
|---|---|---|
| | Without Triazine | *With Triazine |
| 0 | $>10^7$ | $<10^2$ |
| 0.5 | $>1 \times 10^7$ | $<10^2$ |
| 1.25 | $>1 \times 10^7$ | $<10^2$ |
| 2.5 | $1 \times 10^7$ | $<10^2$ |
| 5 | $>1 \times 10^7$ | $<10^2$ |

| Biocide Level (ppm) | Fungal CFU/mL | |
|---|---|---|
| | Without Triazine | With Triazine |
| 0 | $>10^4$ | $10^3$ |
| 0.5 | $>10^4$ | $10^3$ |
| 1.25 | $>10^4$ | $10^3$ |
| 2.5 | $>10^4$ | $10^2$ |
| 5 | $>10^4$ | $10^1$ |

*The bacterial colony counts shown here are the same without n-octylisothiazolone.

The mixture of 10 ppm octylisothiazolone, 800 triazine, and 20 ppm copper as Cu TEA gives a result of $<10^2$ bacteria and $<10^1$ fungi, suggesting that the mixture is complementary in controlling all microbial populations in the fluid. Since the structure and physiology of fungi and bacteria are distinctly different and the activity and application of n-octyl isothiazolone is different, the results obtained with copper and formaldehyde were not expected.

In Summary:
1. Numerous metals both protect an isothiazolone molecule from nucleophilic attack and potentiate its antibacterial activity.
2. Copper triethanolamine, a polyfunctional ligand, is a superior complex in protecting an isothiazolone from nucleophilic attack.
3. Copper triethanolamine potentiates the antibacterial activity of an isothiazolone and a formaldehyde release compound.
4. Copper triethanolamine potentiates the antibacterial activity of an antifungal compound, namely n-octylisothiazolone.
5. A formaldehyde release compound potentiates the antifungal activity of n-octylisothiazolone with the copper triethanolamine. Homologous trilower alkanolamines will also produce such results.

It is intended that the foregoing description be only illustrative of the present invention and that the present invention be limited only by the hereinafter appended claims.

We claim:
1. A composition which suppresses growth of microorganisms which comprises:
   (a) an antimicrobial agent selected from the group consisting of an isothiazolone and a compound which releases formaldehyde;
   (b) copper ion; and
   (c) a trilower alkanolamine wherein alkyl is between 1 and 6 carbon atoms and wherein (b) and (c) form a complex in the solution which enhances suppression of the microorganisms in a solution by the antimicrobial agent compared to a complex of the copper ion and citrate.
2. The composition of claim 1 wherein the trilower alkanol amine is triethanolamine.

3. The composition of claim 1 wherein the ratio of copper ion to trilower alkylamine is about stoichiometric.

4. The composition of claims 1, 2 or 3 wherein the isothiazolone is 5-chloro-2-methyl-4-isolinazolin-3-one.

5. The composition of claim 1, 2 or 3 wherein the antimicrobial agent is n-octyl isothiazolone.

6. The composition of claim 1, 2 or 3 wherein the compound which releases formaldehyde is 1,3,5-hexahydro-tris (2-hydroxyethyl) s-triazine.

7. The composition of claim 1, 2 or 3 wherein the copper ion is between about 1 and 200 ppm in the solution.

8. In a method for providing a solution which suppresses growth of microorganisms in the solution because of an antimicrobial agent selected from the group consisting of an isothiazolone and a compound which releases formaldehyde in the solution, the improvement which comprises:

(a) providing in the solution (1) copper ion; and (2) a trilower alkanolamine wherein alkyl is between 1 and 6 carbon atoms and wherein (1) and (2) form a complex in the solution which enhances suppression of the microorganisms in the solution by the antimicrobial agent compared to a complex of the copper ion and citrate.

9. The method of claim 1 wherein the trilower alkanolamine is triethanolamine.

10. The method of claim 1 wherein the ratio of copper ion to trilower alkylamine is about stoichiometric.

11. The method of claims 1, 2 or 3 wherein the isothiazolone is 5-chloro-2-methyl-4-isolinazolin-3-one.

12. The method of claim 1, 2 or 3 wherein the antimicrobial agent is n-octyl isothiazolone.

13. The method of claim 1, 2 or 3 wherein the compound which releases formaldehyde is 1,3,5-hexahydro-tris (2-hydroxyethyl) 5-triazine.

14. The method of claim 1, 2 or 3 wherein the copper ion is between about 1 and 200 ppm in the solution.

* * * * *